United States Patent [19]

Dorn

[11] 4,212,948
[45] Jul. 15, 1980

[54] APPARATUS FOR DETECTING MICROBIAL PATHOGENS EMPLOYING A CUSHIONING AGENT

[75] Inventor: Gordon L. Dorn, Dallas, Tex.

[73] Assignee: J. K. and Susie L. Wadley Research Institute and Blood Bank, Dallas, Tex.

[21] Appl. No.: 952,339

[22] Filed: Oct. 18, 1978

Related U.S. Application Data

[62] Division of Ser. No. 739,274, Nov. 5, 1976, Pat. No. 4,131,512.

[51] Int. Cl.² .................................................... C12M 1/24
[52] U.S. Cl. ........................................ 435/296; 435/34; 435/803
[58] Field of Search ............... 435/29, 30, 34, 243, 435/253, 254, 255, 261, 296, 299, 803; 210/DIG. 23, DIG. 24; 233/1 R, 26

[56] References Cited

U.S. PATENT DOCUMENTS

| | | | |
|---|---|---|---|
| 3,087,865 | 4/1963 | Drake | 424/93 X |
| 3,519,400 | 7/1970 | Anderson | 210/DIG. 24 |
| 3,875,012 | 4/1975 | Dorn et al. | 435/30 X |
| 3,928,139 | 12/1975 | Dorn | 435/30 X |
| 3,932,222 | 1/1976 | Dorn | 435/30 X |
| 4,131,512 | 12/1978 | Dorn | 435/30 |

*Primary Examiner*—Robert J. Warden
*Attorney, Agent, or Firm*—Richards, Harris & Medlock

[57] ABSTRACT

A method and apparatus are disclosed which provide for improved rapid quantitative analysis of a blood sample for the presence of microbial pathogens. The blood sample is lysed and deposited on a high density, water immiscible, hydrophobic, nontoxic, liquid cushioning agent and subjected to centrifugation. Microbial pathogens contained in the lysed blood sample will collect in a layer adjacent the interface of the cushioning agent and the blood sample residue and, in this concentrated form, can easily be separated from the residual portion of the blood sample for culturing and quantitative counting.

22 Claims, 9 Drawing Figures

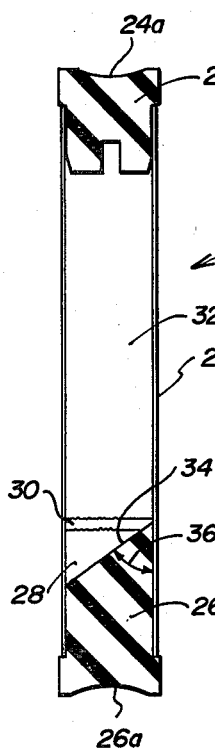
FIG. 1
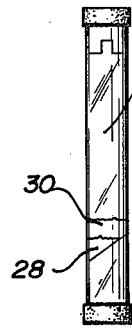
FIG. 2
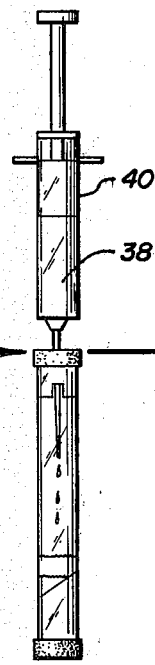
FIG. 3
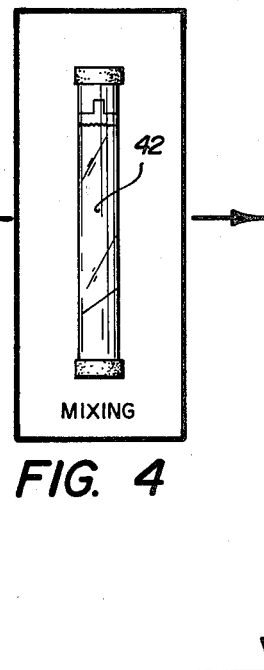
FIG. 4
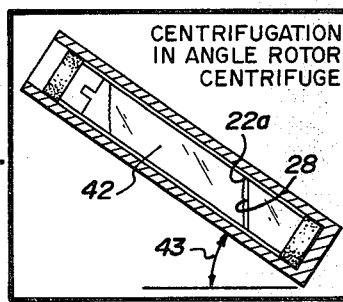
FIG. 5
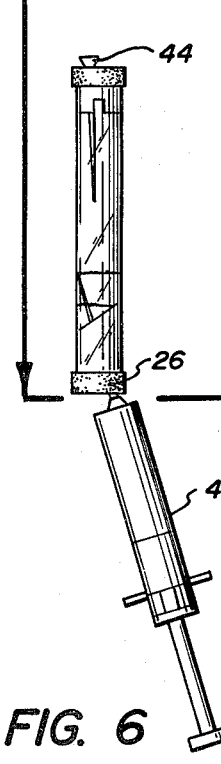
FIG. 6
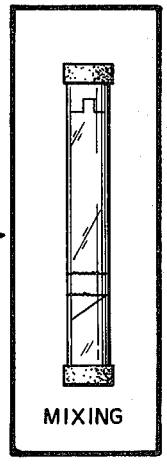
FIG. 7
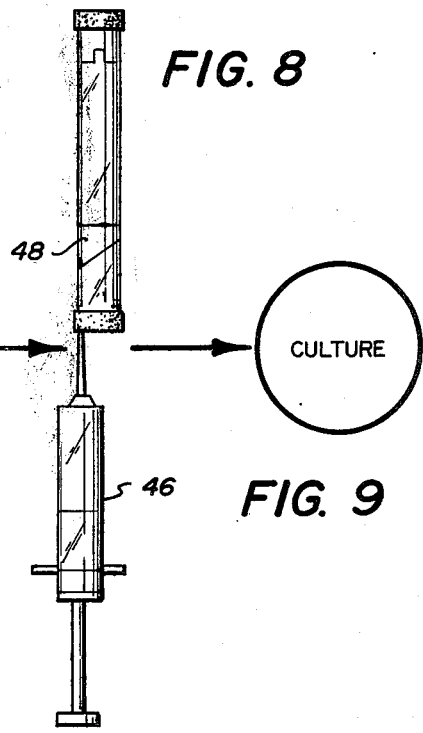
FIG. 8
FIG. 9

APPARATUS FOR DETECTING MICROBIAL PATHOGENS EMPLOYING A CUSHIONING AGENT

This is a division of application Ser. No. 739,274 filed Nov. 5, 1976 now U.S. Pat. No. 4,131,512.

BACKGROUND OF THE INVENTION

This invention relates to a novel method and means for detecting microbial pathogens. In another aspect, this invention relates to a novel technique for selectively separating microorganisms from a sample fluid. In still another aspect, this invention relates to a method of separating microbial pathogens from a lysed blood sample which may contain other components, such as antimicrobial constituents of blood and medicants present in the blood sample without the use of specialized solid or liquid filter media. A further aspect of this invention relates to an apparatus for use in the detection of microbial pathogens which provides improved recovery of microorganisms. In still another aspect, this invention relates to a novel method and apparatus for diagnosing septicemia.

Septicemia, which is the presence of pathogenic microorganisms in the blood, is one of the most serious types of infections encountered. Even though modern medicine has provided an armament of antibiotics and fungal drugs, the mortality rate from septicemia is approximately 25 percent. In addition, when shock accompanies septicemia, the mortality rate increases to over 60 percent. Debilitating diseases, major surgery, administration of immuno suppressive drugs or anti-cancer medication cause patients to be particularly prone to septicemia.

Early administration of appropriate antibiotic therapy is important in fighting septicemia. Consequently, it is imperative that the physician know as rapidly as possible, not only whether the patient has septicemia, but also the identity of the affecting microorganisms and the susceptibility of the microorganisms to antibiotic agents. Thus, proper and timely diagnosis of septicemia depends upon very rapid and efficient quantitative analysis of the patient's blood. Further, it is imperative during the quantitative analysis of the patient's blood that the blood sample not be contaminated with pathogens from the laboratory environment.

Three analytical systems have been conventionally utilized to determine the presence of microorganisms in a body fluid. These conventional systems include the liquid broth culture technique, the so-called pour plate method and the filtration method using a solid matrix filter. Each of these systems has its drawbacks, and none of the systems provide for rapid detection of microorganisms in the blood sample. Generally, the liquid broth method is not quantitative, and the pour plate method and filtration method (using a solid matrix filter) are open systems subject to external contamination, e.g., the introduction of pathogens into the culture by the laboratory atmosphere and personnel.

Recently, an improved method and apparatus has been developed for determining the presence of microbial organisms within a sample fluid including, for example, blood. This method is disclosed in U.S. Pat. No. 3,928,139, issued Dec. 23, 1975 and entitled "Detection of Microbial Pathogens". According to this improved method, rapid and quantitative detection of microbial pathogens from a sample of body fluid is provided by employing a liquid filter medium. The sample fluid is placed on the liquid filter medium within a confined sterile zone. The liquid filter medium has a density greater than the sample fluid and comprises a sterile aqueous solution which will selectively receive microbial pathogens from the sample fluid. The confined sterile zone is thereafter subjected to centrifugation to force the sample fluid against the liquid filter medium and cause microbial pathogens to selectively pass therein and thereby separate from the mass of the body fluid sample. Next, the liquid filter medium containing the microbial pathogens is separated from the remainder of the sample fluid and portions of the liquid filter medium are subjected to various culturing conditions.

The improved method described above does provide a very rapid and efficient procedure for separating microbial pathogens from a sample fluid. According to the preferred embodiment of the liquid filter medium method, the blood sample is lysed prior to the centrifugation step which causes the microbial pathogens to be selectively received by the liquid filter medium. Other pretreating agents, such as anti-coagulating agents are also used to prepare the blood sample. Some ingredients of the preferred liquid filter media employed by the improved method discussed above are incompatible with some of the pre-treating and/or lysing agents. Furthermore such agents will admix with the liquid filter medium if added thereto prior to the time that the blood sample is added to the confined sterile zone, and once so admixed such agents cannot defuse from the liquid filter medium rapidly enough to effectively treat the blood. Therefore, it is necessary either to subject the blood samples to the possibility of external contamination by admixing the blood sample with the pre-treating and/or lysing agents prior to introducing the sample into a closed sterile system or to employ a specialized apparatus whereby the treating agents may be contained within the closed system but separate from the liquid filter medium until the apparatus is placed into use. Apparatus of this type are disclosed in U.S. Pat. No. 3,875,012, issued Apr. 1, 1975, and entitled "APPARATUS AND METHOD FOR THE DETECTION OF MICROBIAL PATHOGENS" and in U.S. Pat. No. 3,932,222, issued on Jan. 13, 1976 and entitled "FOR ISOLATING PATHOGENIC MICROORGANISMS".

Furthermore when using the above-described improved method for detecting microbial pathogens in blood samples using a liquid filter medium in a centrifugation vessel which includes an injectable closure means at the end of the vessel against which the blood sample and liquid filter medium are forced by centrifugation. It has been discovered that some of the heavier microbial pathogens which are received by the liquid filter medium can pass, under the force imparted by centrifugation, completely through the liquid filter medium and come to rest adjacent the bottom of the centrifugation vessel being employed, and unless great care is taken during separation and recovery of the liquid filter medium some of such microbial pathogens can be left behind, unrecovered. It is believed that the loss of microbial pathogens, in such cases, occurs because, upon passing completely through the liquid filter medium, the microbial pathogens become lodged in the tiny crevice formed between the wall of the centrifugation vessel and the injectable closure means.

Thus, it is desirable to have a closed, sterile method for separating and concentrating microbial pathogens suspected to be present in a blood sample without the necessity of having to premix the blood sample in a potentially contaminating environment and without the necessity of employing specially designed apparatus for accomplishing the pretreating step of the procedure. Furthermore, it is especially desirable to increase recovery of the microbial pathogens which have been selectively separated and concentrated from a sample fluid.

SUMMARY OF THE INVENTION

According to one embodiment of the present invention, a method of detection of microbial pathogens suspected to be contained in a sample fluid is provided. The procedure can be utilized on all types of body fluids, such as blood, bone marrow, spinal and pleural fluids, urine, and the like. In addition, the procedure can be utilized on any sample containing microorganisms to concentrate and separate the microorganisms from any antimicrobial factors present in the sample fluid, for example, foodstuff, such as milk, and the like. Generally, when employed in connection with a blood sample the method includes depositing a lysed blood sample on a relatively thin layer of a high density, non-toxic, water immiscible, hydrophobic, liquid cushioning agent. Such cushioning agent is compatible with lysing and other blood heating agents and such agents will rapidly separate from said cushioning agent when admixed therewith. Therefore, preferably, to avoid possible contamination, a blood sample may be injected into a sterile confined zone containing both the cushioning agent described above and an effective amount of lysing and/or other blood treating agents so that the blood sample is treated in situ. The lysed blood sample contained within the confined sterile zone is then subjected to centrifugation which forces the blood sample against the cushioning agent also contained therein. It has been discovered that upon such centrifugation, substantially all the microbial pathogens contained in a lysed blood sample will pass out of suspension and collect in a layer adjacent the interface of the cushioning agent and the blood sample itself. The microbial pathogens will actually penetrate the interface between the cushioning agent and blood sample and enter the cushioning agent or will remain on the surface or adjacent the surface of the cushioning agent and none or substantially none will pass completely through the cushioning agent. This is to be contrasted with the use of a liquid filter medium which selectively receives microbial pathogens and through which some of the microorganisms may pass completely and become entrapped between the wall of the centrifugation vessel and injectable closure means. The layer of microbial pathogens which so forms in accordance with the subject invention can then be recovered without substantial loss by separating the cushioning agent and a minor portion of the residual blood sample adjacent the interface with the cushioning agent from the major portion of the sample. Thus, the presence of the cushioning agent during centrifugation of the lysed blood sample allows microbial pathogens to be separated from the lysed blood sample as well as from any medicaments and antipathogenic factors contained therein. Upon recovery, the microbial pathogens can be analyzed both quantitatively and qualitatively.

Thus, in accordance with the present invention a high density, non-toxic, water immiscible, hydrophobic liquid cushioning agent for the collection and separation of microbial pathogens from a sample fluid in a centrifugation zone is provided. I have discovered that the use of such a cushioning agent either alone or in conjunction with a liquid filter medium provides for a substantial increase in the recovery of microbial pathogens which have been separated from a blood sample. Generally, inert liquids which are non-toxic to microbial organisms and which are water immiscible, hydrophobic and of high density can be used as cushioning agents. The term "high density" as applied herein refers to a liquid which is of a density sufficient to not be supported by a mixture of a blood sample and treating fluid therefor, or any other fluid sample suspected of containing microbial pathogens in the presence of centrifugal force. It is believed that these cushioning agents because of their high density provide a cushioning effect to microbial pathogens which are forced to pass out of suspension in a blood sample upon centrifugation. The microbial pathogens are caught, and cushioned adjacent the interface between the blood sample itself and the cushioning agent. In this manner, microbial pathogens are not lost to interstitial spaces which may be present on the surface of the confined sterile zone against which they have been forced by centrifugation.

In a further embodiment of the present invention, a novel article is provided for recovering microbial pathogens from a sample fluid. The novel article comprises a smooth continuous surface within a centrifugation receptacle such that on centrifugation of the centrifugation receptacle the sample fluid being centrifuged will be forced against the surface at a substantially perpendicular angle. The surface comprises the inner end of an injectable closure means for the receptacle, which has said above described cushioning agent positioned thereon. Said cushioning agent will become distributed on the inner surface of said injectable closure means and will fill the interstitial space between the wall of the centrifugation vessel and the injectable closure means to prevent entrapment of any of the heavier microbial pathogens that may pass to said cushioning agent during centrifugation. When a swinging bucket type centrifuge is utilized, the inner surface of said injectable closure means should be perpendicular to the bottom of said injectable closure means. Furthermore, when an angle rotor type centrifuge is employed, the smooth inner surface of the injectable closure means is positioned within the centrifugation receptacle at an angle which is the complement of the angle at which centrifugation is to be performed. This unique design enables one to use the commonly available angle centrifuges and actually results in a shorter path length of travel for the pathogen through the sample fluid before it becomes concentrated adjacent the inner face of the cushioning agent. This shorter path length results in a greater average force ("g" force) to be applied on the microbial pathogens within the sample fluid. Centrifugation with this unique designed centrifugation vessel will result in the pathogens being concentrated adjacent the interface of the cushioning agent and the sample fluid and partially on the sidewall of the centrifugation container. The microbial pathogens thus concentrated are easily collected and removed from the centrifugation vessel. Thus, the positioning of the surface within the centrifugation receptacle at an angle such that the blood sample and cushioning agent will be forced against the surface at a substantially perpendicular angle during centrifugation, insures that the cushioning agent will be disposed substantially uniformly across the surface so as to completely seal any interstitial spaces which will trap microbial pathogens. Such arrangement provides a shorter path length of travel for pathogens and therefore a greater average "g" force to be imparted upon pathogens to provide a more efficient concentrated deposit thereof which can be easily removed from the centrifugation vessel. Furthermore, the use of this specially designed centrifugation vessel results in an increase centrifugation efficiency in that centrifugation can be carried out at less g's within the same time period as in conventional centrifugation or at the same g's in a shorter time period than the conventional procedure.

Furthermore, in accordance with a preferred embodiment of the subject invention, blood lysing and other blood treating agents which are employed to prepare a blood sample can be positioned in an aqueous solution within the centrifugation vessel in contact with the liquid cushioning agent. The liquid cushioning agent is of a higher density than said aqueous solution, and is hydrophobic and water immiscible and will thereby support such aqueous solution. Furthermore, if the centrifugation vessel becomes agitated during storage and shipment, the lysing or other blood treating agents will admix with the cushioning agent. However, once the centrifugation vessel is subjected to centrifugation the high density liquid cushioning agent readily separates (sediments) and allows the blood treating agents to admix with the blood sample within the vessel. This is a great advantage over the above-described conventional liquid filter media which have ingredients which are incompatible with some of the blood treating agents and furthermore since the conventional liquid filter media are aqueous based, they will admix with the aqueous based blood treating agents if the two are in contact and prevent them from effectively diffusing therefrom and treating a blood sample which is positioned within the vessel.

DETAILED DESCRIPTION OF THE INVENTION

This invention can be more easily understood from a study of the drawings in which:

FIG. 1 is a cross sectional view of the preferred centrifugation article of the present invention; and FIG. 2–9 depict the steps of the improved method for detection of microbial pathogens employing the article of FIG. 1.

Now referring to FIG. 1, a preferred embodiment of the improved centrifugation article of the present invention will be described. As shown, the article 20 comprises an elongated, tubular centrifugation vessel 22 having a conventional injectable closure member 24 which sealably closes the upper end thereof, and a novel injectable closure member 26 which sealably closes the lower end thereof. When article 20 is to be employed in the preferred embodiment of the method of detecting microbial pathogens of the present invention, an effective amount of cushioning agent 28 and blood treating agents 30 can be deposited therein.

Centrifugation vessel 22 can be made of siliconized glass or hard plastic, such as polycarbonate or polypropylene. Injectable closure members 24 and 26 can comprise rubber self-sealing stoppers. Injectable closure members 24 and 26 both carry indentations *24a* and *26a*, respectively, to enhance the ease of injection by common types of medical injection needles. Evacuated space 32 is maintained at a lower than atmospheric pressure at a predetermined value so that the centrifugation vessel can receive a known amount of liquid by injection through injectable closure member 24 without excessive pressure being built up within the interior thereof which would cause injectable closure members 24 and 26 to become dislodged from the openings within centrifugation vessel 22.

Referring especially to injectable closure member 26 at the lower end of centrifugation vessel 22, it is noted that inner surface 34 of injectable closure member 26 is positioned at an angle with respect to the walls of centrifugation vessel 22.

It is noted that article 20 is especially designed to be utilized within an angle rotor centrifuge and that the angle of inner surface 34 is a complement of the angle of the rotor. It should be noted, however, that the device of the subject invention can be utilized in a conventional swinging bucket type centrifuge. In the latter instance, surface 34 should be perpendicular to the bottom of the article 20 and is otherwise utilized in the same general manner as will be described hereinbelow for the article 20 illustrated in FIG. 1. Surface 34 should be smooth and substantially free of interstitial spaces and crevices in which microbial pathogens could be entrapped. Further, the circular sealing area around surface 34 where the material of injectable closure member 26 meets the walls of the centrifugation vessel 22, should be tightly sealed so that the interface does not provide a large circular crevice in which microbial pathogens could become lodged.

The angle of incline of smooth surface 34 with respect to the walls of centrifugation vessel 22 is determined according to the centrifugation apparatus in which article 20 is to be centrifuged.

As discussed above, when a swinging bucket type centrifuge is utilized, surface 34 will be positioned perpendicular to the bottom of the article 20. However, when an angle rotor centrifuge is utilized, surface 34 will carry the complement of the angle of the rotor. Therefore, in general when the rotor angles range from about 60 degrees to 10 degrees, the angle of surface 34, or angle of incline 36 within the centrifugation vessel will range correspondingly from 30 degrees to 80 degrees. Thus, the angle of incline, depicted by arc 36, will generally be the complement of the angle at which device 20 rests within the centrifuge during centrifugation. For example, the angle of incline 36 depicted in FIG. 1 is approximately 34 degrees. Thus, for example, when article 20 is placed in an angle rotor centrifuge in which centrifugation occurs at approximately 56 degrees, fluids contained within article 20 will be forced against surface 34 at a substantially perpendicular angle.

It should be noted that as depicted in FIG. 1, injectable closure member 26 is formed from a single piece of rubber. However, surface 34 can be provided by employing a plug of material adjacent to the inner surface of a common rubber stopper such as injectable closure member 24, for example. Such a plug can be manufactured from any of a number of materials which provide a smooth surface, a good seal with the wall of centrifugation vessel 22, are injectable and which are non-toxic to microbial pathogens. A method of fabricating such a plug is to do so in situ by employing a material which can be poured into centrifugation vessel 22 once a common rubber stopper, such as injectable closure member 24, has been placed in the lower end of centrifugation vessel 22. The material should be fluid enough and have setting times long enough to allow centrifugation vessel 22 to be placed at the desired angle of incline with the result that the material flows to the desired angle of incline and then sets. Upon setting, the material will provide a smooth surface 34 and a good seal with the walls of centrifugation vessel 22. Examples of such materials are common bathtub caulks and silicone base resins which are provided in a low viscosity liquid from and which cure to form an elastomeric material. An example of the latter type of material is a silicone based fluid resin sold under the trade name SYLGARD 134 by Dow Corning, Midland, Mich. When a material such as SYLGARD is employed, it is sometimes advisable to use a primer on the interior wall of centrifugation vessel 22 in order to insure a good seal between the cured SYLGARD and the centrifugation vessel wall 22. A suitable primer is sold under the trade name DC 1200 by Dow Corning. Thus, for example, smooth inclined surface 34 which is depicted in FIG. 1 as the inner surface of a unitary injectable closure member 26 can be prepared by priming the interior wall of centrifugation vessel 22 with a suitable silicone base resin primer such as DC 1200, inserting a common rubber stopper such as that depicted as injectable closure member 24, pouring an amount of a liquid silicone base resin such as SYLGARD 134 into centrifugation vessel 22, placing the entire vessel at the desired angle of incline and curing the silicone resin under appropriate conditions to form an elastomeric plug having a smooth surface 34 positioned at the desired angle of incline adjacent a common rubber stopper. Bathtub caulking and similar materials may be employed in the same general manner, if desired, and the correct angle of incline may be formed by centrifuging the article containing the uncured plug forming material in the type of centrifuge with which the article is to be employed.

Once smooth surface 34 has been formed either by placement of a unitary injectable closure member 26 or by a combination of a rubber stopper and a plug of material as described above, as effective amount of the cushioning agent of the subject invention can be added to the article 20. The amount of cushioning agent employed should be sufficient to completely cover surface 34 upon centrifugation but not so large as to significantly limit the amount of blood which article 20 can receive. The amount of cushioning agent utilized can vary with the parameter of the particular system chosen, for example the stoppers design, volume of the residual blood and volatility of the cushioning agent utilized. A preferred amount of cushioning agent can comprise from about 3.3% to about 30.0% by volume based on the volume of the cushioning agent-residual blood sample mixture which is removed from article 20 and tested for the presence of microbial pathogens.

Generally, the cushioning agent of the subject invention can comprise a high density, hydrophobic, water immiscible liquid. As noted previously, the term "high density" as used herein refers to a liquid which wll not be supported by the mixture of blood and blood treating fluid or any other sample fluid suspected of containing microbial pathogens in the presence of centrifugal force. In addition, the cushioning agent should be non-toxic to microbial pathogens and relatively inert with respect to butyl rubber, silicone rubber and other types of elastomers employed in the manufacture of the injectable closure members described above. The density of the cushioning agent can be in the range of from at least about 1.2 grams per cubic centimeter to about 2.0 grams per cubic centimeter with the preferred range being from about 1.6 grams per cubic centimeter to about 2.0 grams per cubic centimeter. Generally, fluorinated hydrocarbons having the above described characteristics and having molecular weights in the range of from about 300 to about 850 are preferred. Furthermore, fluorinated hydrocarbons having the above qualities which will evaporate at approximately the same rate as water once a sample containing the cushioning agent is placed on a common type of culture plate are preferred. Therefore, cushioning agents having the above described qualities and boiling points of at least about 200 degrees F. to about 420 degrees F. and preferably of about 225 degrees F. to about 280 degrees F. can be utilized. The cushioning agent should also have a vapor pressure which will not disrupt the injectable closure means from the tube during manufacturing steps such as autoclaving, for example. Fluorinated hydrocarbons sold under the trade name FLUORINERT by 3M Company of Minneapolis, Minn., have been found to perform well as cushioning agents. Specifically, types FC-75, FC-48, and FC-43 of the FLUORINERT series have been found to be especially useful.

Although the exact function which such cushioning agents perform is not fully known, it is believed that they improve collection of microbial pathogens which have passed from suspension in a centrifuged blood sample in at least two ways. First, the cushioning agent serves to seal interstitial spaces, cracks, and crevices both on the smooth surface 34 of the centrifugation vessel 22 and at the interface between the walls of the centrifugation vessel 22 and injectable closure member 26. Thus, microbial pathogens which might otherwise become entrapped in such interstitial spaces, and therefore not recovered, are recovered with the cushioning agent 28 when it is removed from article 20. Secondly, it is believed that the cushioning agent does act to cushion the impact of microbial pathogens which are forced out of suspension in a blood sample during centrifugation. This cushioning effect reduces the danger of injury to microbial pathogens which might otherwise occur upon impact. Further, while some of the microbial pathogens may actually pass into the cushioning agent substantially none will pass completely through it and a majority will form on its surface at the interface between the cushioning agent 28 and the blood sample and collect in a layer.

After the cushioning agent 28 has been deposited within centrifugation article 20, water soluble treating agents 30 for the blood may also be deposited therein. Such treating agents can include, for example, lysing agents and/or anticoagulants. Any suitable lysing agent can be utilized so long as it is non-toxic to microorganisms. A suitable such lysing agent is an aqueous solution of a non-toxic saponin. It must be noted that many saponins are known to be toxic to microbial pathogens. However, as set forth in Applicant's patent U.S. Pat. No. 3,883,425, issued May 13, 1975, and entitled "DETOXIFICATION OF SAPONINS", which is herein incorporated by reference, a method is disclosed for removing the toxic ingredients from the heretofore thought to be toxic saponins. In general, the toxic saponin material can be detoxified in accordance with the invention set forth in that patent and the resulting purified material used within the scope of this invention. In addition, the aqueous solution of saponin can contain an anticoagulant and/or oxygen scavenger. A preferred anticoagulant is sodium polyanethol sulfonate (SPS) or heparin, for example. Sodium polyanethol sulfonate is preferred because it not only acts as an anticoagulant but also inhibits the phagocytic activity of granulocytes and monocytes and the normal antibacterial activity of blood serum. It is preferred that said aqueous solution of treating agent be at least 1.0% by volume of the total liquid in centrifugation vessel 22 including the treating solution, sample fluid and cushioning agent and preferably from about 7.6% to about 17.5% by volume thereof.

Once the treating agents 30 have been deposited in centrifugation article 20, injectable closure member 24 can be put in place and space 32 evacuated to the desired lower than atmospheric pressure.

Now referring to FIGS. 2–9, an analysis sequence is schematically depicted illustrating a preferred embodiment of the subject invention. As an example, a procedure which is carried out in accordance with one embodiment of this invention for detection of microbial pathogens within a blood sample can be carried out conveniently with the following apparatus:

The above described centrifugation article 20 containing the cushioning agent 28 and blood treating agents 30—the vessel can be of 12-14 milliliters in volume.

A sterile glass syringe and one 1½ inch 18 gauge disposable hypodermic needle;

One sterile glass syringe and one 1 inch 21 gauge disposable hypodermic needle;

One ⅝ inch 25 gauge hypodermic needle with cotton inserted at its hub (used as a vent);

Three blood agar plates;

One chocolate agar plate;

One Sabouraud plate.

It is noted that with the exception of centrifugation article 20 or some equivalent article, various types of well-known laboratory apparatus and culture media can be used to carry out the novel process of the subject invention. It is particularly noted that the culture media set forth above are exemplary only and are generally preferred to be utilized for detecting the most commonly known microbial pathogens. The blood agar plates suggested are conventionally utilized blood agar plates which are basically sheeps blood and a base nutritional agent such as sugar, which is held together with an agar solidifying agent on a Petri plate. The chocolate agar plate is designed to grow certain fastidious pathogens, e.g., hemophilus. The Sabouraud plate is specifically designed to grow fungi.

Thus, while various apparatus can be utilized in the method of the subject invention, the above list of apparatus and materials can be conveniently utilized in the scope of this invention in a manner set forth below.

To utilize centrifugation article 20 set forth in FIG. 1 in the drawing, it is initially positioned so that injectable closure member 26 with its smooth angled surface 34 is at the lower end of article 20 so that the cushioning agent 28 and blood treating fluid 30 rest upon smooth angled surface 34. It should be noted that for purposes of illustration two separate liquid levels are depicted in FIG. 2 representing the cushioning agent 28 and treating fluid 30. In practice, a non stable emulsion or mixture of these two fluids may occur due to handling so that two distinct liquid layers may not always be present. This unstable mixture of cushioning agent 28 and blood treating fluid 30 in no way adversely affects the method set forth herein since separation of the two fluids rapidly occurs upon centrifugation.

Next, a predetermined amount of a blood sample 38 drawn from the patient, for example 7 milliliters of blood, is injected into the evacuated space of centrifugation article 20 as depicted in FIG. 3 using a common type of syringe 40. Alternately, the sample can be drawn directly into article 20 using a standard and double needle fixture supplied with conventional vacuum blood drawing devices such as sold under the mark "Vacutainer" by Beckten Dickenson. Then, article 20 containing the blood sample 38, the blood treating fluid 30, and the cushioning agent 28 is subjected to mixing to insure that the blood treating agents 30 are completely admixed with the blood sample 38. This mixing step is depicted schematically by FIG. 4.

After the blood sample 38 has been treated in this manner, centrifugation article 20 is centrifuged to cause the microbial pathogens within the treated blood sample 42 to pass out of suspension and collect adjacent the interface of the high density cushioning agent 28 and the residual of the sample fluid. Some microbial pathogens will actually be deposited upon the sidewall of centrifugation vessel 22 adjacent the high end of smooth surface 34 at point 22a. This centrifugation step is represented schematically by FIG. 5. The speed and time of centrifugation can vary widely depending upon the construction material of centrifugation article 20 and the type of centrifugation apparatus. The centrifugation can be conveniently accomplished by imparting from between about 1500 and 6000 gravities and preferably from about 1500 to 3000 gravities to the centrifugation article 20 containing the treated blood sample 42 and cushioning agent 28. As depicted in FIG. 5, an angle rotor centrifuge is employed which places the centrifugation article 20 at an angle of 56 degrees for example, (depicted by arc 44) during centrifugation. Thus, if smooth angled surface 34 is at a 34 degree angle with respect to the interior walls of centrifugation article 20, the treated blood sample 42 and cushioning agent 28 will be forced against smooth angle surface 34 at a relatively perpendicular angle during centrifugation. It is noted that when a swinging bucket type of centrifuge is employed, centrifugation article 20 will be centrifuged at substantially 0 degrees with respect to a horizontal surface. Thus, in such a case the angle of surface 34 will be approximately 90 degrees and an injectable rubber closure member having a flat inner surface can be substituted for injectable closure member 26.

Once the centrifugation step has been completed, centrifugation article 20 can be removed from the centrifuge and the major portion of the treated blood sample 42 from which microbial pathogens have been separated can be removed. It is noted that, as used herein, the term "residual treated blood" or "residual blood" refers to a blood sample which has been centrifuged such that the microbial pathogens present therein have collected at the bottom of the sample, hence, leaving the "residual" portion of the sample substantially free of microbial pathogens. This step is depicted in FIG. 6. To aid in ease of removal, a vent needle 44 in the form of a common hypodermic needle with cotton in its hub, for example, is injected through injectable closure member 24. A second hypodermic needle with syringe 45 attached can then be injected through injectable closure member 26 to remove a major portion of the residual treated blood sample 42 from which microbial pathogens have been separated. For example, when the centrifugation vessel has a volume of from 12 to about 14 milliliters, a 1½ inch 18 gauge needle can be employed to remove all but about 1.3 to 1.7 milliliters of the treated blood sample 42. As shown, it is preferred that the major portion residual blood sample be drawn from the interior of centrifugation vessel 22 at a point opposite the sidewall adjacent the upper bevel end of smooth surface 34 to avoid disturbing the layer of microbial pathogens which has formed on and within the interface of the two liquids and on the sidewall of centrifugation vessel 22 adjacent the upper end of said beveled smooth surface 34. The majority of the residual blood is removed in this step however, a small portion of the residual blood should be left in the centrifugation vessel 22 such that of the total fluid remaining, the cushioning agent comprises from about 4.7% to about 28.8% by volume. It is preferred that no more than about 20% by volume shall be said cushioning agent because greater quantities of said cushioning agent may deleteriously effect the morphology of microbial pathogen colonies in subsequent pathogen growth steps used in the process.

Once the major portion of the treated residual blood sample has been removed, both needles may be withdrawn from injectable closure members 24 and 26, and centrifugation article 20 is then subjected to a second mixing step depicted schematically by FIG. 7. However, if desired, vent needle 44 can be left in its position through injectable closure member 24 to assist in removal of the pathogen containing fluid in a later step. The second mixing step serves to resuspend microbial pathogens which have separated from the major portion of residual treated blood sample 42 and which have formed the layer described above. Resuspension of the microbial pathogens so collected in the remaining minor portion of the residual treated blood sample 42 insures greater and more uniform recovery.

Once the mixing step has resuspended the microbial pathogens in a minor portion of the residual treated blood sample 42, the mixture of microbial pathogens in the residual treated blood sample and the high density cushioning agent can be removed from centrifugation article 20. This step is depicted in FIG. 8. As noted above, if desired, the venting hypodermic needle 44 may be inserted through injectable closure member 24 to allow easier removal of the remaining constituents. The syringe 46 with attached hypodermic needle can then be injected through injectable closure member 26 to draw out the mixture 48 of cushioning agent 28, minor remaining portion of residual blood sample 42 and microbial pathogens present therein. It is noted that particularly good recovery can be obtained if the hypodermic needle used to remove these constituents is injected at the lower end of the angled smooth surface 34. It is believed that the angle of surface 34 acts, in part, as a funnel into which the remaining fluid containing the microbial pathogens flow. The mixture 48 of high density liquid cushioning agent 28, and the remaining minor portion of the residual treated blood sample 42 with the recovered microbial pathogens should be approximately 1½ milliliters of fluid. This fluid is then distributed on bacterial growth media. This step is schematically illustrated in FIG. 9 in the drawing. With the apparatus set forth above, the material can be distributed as follows:

One blood agar plate can receive 0.3 milliliters of the mixture and the plate can be incubated at 36 degrees C. in an aerobic atmosphere. Two blood agar plates can receive 0.3 milliliters of the aqueous solution and can be incubated at 36 degrees C. in an anaerobic environment. One chocolate agar plate can receive 0.3 milliliters of the aqueous solution and can be incubated at 36 degrees C. in a candle jar. The Sabouraud plate can receive 0.3 millilters of the mixture and can be incubated at 25 degrees C. in an aerobic environment. The growth media should be checked daily for the presence of colonies. Microscopic analysis techniques can be employed. The number of microbial pathogens in one milliliter of the blood can be determined by multiplying the number of colonies by a correction factor. This correction factor takes into consideration the recovery rate for a given organism, the volumes of blood and high density cushioning agent employed and the amount of final mixture plated. In the general example set forth above, the correction factor is 1.4.

It should again be noted that the exact procedural steps, apparatus and equipment, and types of culture media utilized in the detailed embodiment set forth above, can vary as desired. For example, any known means can be utilized to admix the blood sample with the anticoagulant and/or lysing agent. Furthermore, in some cases, the step of withdrawal of the major portion of the blood sample 42 depicted in FIG. 6 can be eliminated completely and only a minor portion of the blood sample 42 containing resuspended microbial pathogens can be withdrawn from the bottom of the centrifugation article 20 along with the high density cushioning agent 28 as depicted in FIG. 8. Various other modifications can be used in the procedure as desired.

EXAMPLE

The following example is given to better facilitate the understanding of this invention and is not intended to limit the scope thereof.

This example was performed in order to establish comparative data regarding the percent recovery of microbial pathogens from blood samples when the liquid filter medium technique set forth in Applicant's previous patent, U.S. Pat. No. 3,928,139, entitled "PROTECTION OF MICROBIAL PATHOGENS" issued Dec. 23, 1975, was employed as compared to recoveries of microbial pathogens obtained by employing the cushioning agent technique of the present invention.

The techniques employed in this example are identified in Table I as either "Liquid Filter Medium" or "Cushioning Agent". The information appearing in parenthesis directly beneath the technique identification sets forth the liquid filter medium employed (e.g., 50% Sucrose) in the liquid filter medium tests and the cushioning agent employed (e.g., Fluorinert FC-48) in the cushioning agent tests. Each sample tested (1-21 as listed in Table I) was prepared from 7 milliliter samples of sterile lysed blood from healthy blood donors each sample being inoculated with 0.3 milliliters of various known concentrations of a human pathogen (either *Escherichia coli* or *Candida albicans* as designated in Table I).

In each of the sample tests performed, a centrifugation article 20 as shown and described above was employed whether the liquid filter medium technique or the cushioning agent technique was being used. In order to investigate the effect of employing a surface disposed at substantially the complement of the angle at which article 20 is centrifuged, some of the article 20 employed rubber stoppers having flat, smooth inner surfaces so that the inner surface of the bottom stopper was horizontal with ground level when article 20 was standing upright. These bottom stoppers are identified as "Horizontal" in Table I. Also employed were specially fabricated bottom closure members prepared by using common rubber stoppers in conjunction with either common bathtub caulk or a silicone based resin sold under the trade name of SYLGARD 134 by Dow Corning, Midland, Mich., to thereby prepare a bottom surface within article 20 which, with respect to the walls of article 20, would have an angle substantially equal to the complement of the angle at which article 20 was centrifuged. Samples tested using centrifugation articles employing the angled bottom stopper are identified as such in Table I and the material employed (either bathtub caulk or SYLGARD) to prepare the angled surface is also set forth. The centrifugations performed in conjunction with each of the samples listed in Table I employing the angled bottom stopper were performed in an angle rotor centrifuge wherein the angle of centrifugation was approximately 56 degrees. Thus, those centrifugation articles comprising angled bottom stoppers (angled at approximately a 34 degree angle) presented a bottom surface at a substantially perpendicular angle to the direction of the centrifugal force. Further, those samples employing a horizontal bottom stopper (as identified in Table I) were centrifuged in a swinging-bucket type centrifuge, which during operation causes centrifugation article 20 to be spun in a plane substantially parallel with that of the ground. Thus, centrifugal force was exerted in a direction substantially perpendicular to the surface of the horizontal bottom stoppers.

When the liquid filter medium technique was employed, each of the articles 20 contained 1.2 milliliters of an aqueous solution containing 1.5 weight percent gelatin and the concentration by weight of sucrose indicated in Table I. Each of the articles 20 was inverted and chilled to 4 degrees C in an inverted position before the inoculated blood sample was added. After each of the articles 20 had received the requisite amount of the blood sample containing the known amount of human pathogen, it was placed within a water bath while still inverted. The water bath was set at 42 degrees C and the gelatin was allowed to melt. Each tube was then centrifuged at approximately a 56 degree angle in a rotor centrifuge. Centrifugation was for a 30 minute period and was carried out at a relative centrifugal force of 1500 or 3000 gravities as indicated in Table I.

At this point in the procedure used in conjunction with some of the samples (hereinafter described as the "3" entry procedure), a 10 milliliter syringe was inserted through the bottom stopper to remove about 6.7 milliliters of residual blood sample. Then, centrifugation article 20 was subjected to mixing in a vortex mixer for about ½ to 2 minutes. After the mixing step, 1.5 milliliters of the admixed filter medium and that portion of the blood sample remaining in article 20 were removed by a common syringe with attached needle. In other samples, the step of removing a major portion of the residual blood sample after centrifugation was not employed. In this case 1.5 milliliters of the liquid filter medium and blood sample adjacent the bottom stopper were withdrawn from the bottom of centrifugation article 20 directly after centrifugation. The 1.5 milliliters, comprised of a mixture of liquid filter medium and residual blood sample as well as the collected microbial pathogens, was then admixed, after withdrawal from article 20, in order to provide a relatively even distribution of the components upon plating of the sample. The difference in these two procedures is indicated in Table I under the notation "Number of Entries" which designates each test sample as following the procedure having either two or three entries. In the case of three entries, the first entry is for injection of the blood sample, the second entry is for the removal of the majority of the blood sample after centrifugation but before mixing, and the third entry is for removal of the remaining liquid filter medium and the remaining portion of the blood sample. In the two entry procedures, the first entry is for injection of the blood sample into article 20 and the second entry is for withdrawal from the bottom of the centrifugation article 20 of approximately 1.5 milliters of admixed liquid filter medium and blood sample.

In both cases, whether the two entry or three entry procedure was employed, five samples containing 0.3 milliliters each of the 1.5 milliliters drawn from the bottom of article 20 was plated on 5 separate plates. After incubation, these samples were compared with control plates prepared by adding the same known quantity of microbial pathogens as was injected into the tested blood sample to a saline solution and plating 0.3 milliliters of this saline solution on each of 5 agar plates. The percent recovery based on the comparison of the sample plates to the control plates is listed in Table I.

The procedure used with regard to each sample of blood tested using the cushioning agent technique was as follows. A centrifugation article 20 was prepared using either a horizontal or angled bottom stopper as discussed above. Each centrifugation article 20 used in the cushioning agent procedure contained 0.3 milliliters of Fluorinert FC-48. Seven milliliters of lysed blood which had been contaminated with a known number of microbial pathogens was then injected through the top stopper of article 20. The next step was to centrifuge each of the articles 20 in the same angle rotor centrifuge employed in the liquid filter medium technique. Centrifugation time was 30 minutes and the relative centrifugal force applied was either 1500 gravities or 3000 gravities as shown in Table I. When the 3 entry technique was employed, approximately 5.8 milliliters of residual blood sample was withdrawn by injection of a 10 milliliter syringe through the bottom stopper. When the two entry system was employed, no such entry or withdrawal was made. In either case 1.5 milliliters, comprising approximately 1.2 milliliters of residual blood sample and 0.3 milliliters Fluorinert was withdrawn from the bottom of centrifugation article 20. Five sample plates were then prepared utilizing 0.3 milliliters of the admixed residual blood sample and Fluorinert in each case. These sample plates were incubated and subsequently compared with control plates which had been prepared in the same manner as discussed above in connection with the liquid filter medium technique. The percent recovery when employing the cushioning agent technique was then computed and is set forth in Table I.

While an exact theory to explain the data obtained pursuant to this experiment cannot be set forth, it is believed that the results obtained support Applicant's theory with regard to the present invention. For example, the low recovery rate of Sample No. 2 of Table I (wherein the liquid filter medium technique was employed using 50% sucrose and a horizontal bottom stopper) could be a result of microbial pathogens becoming trapped along the interior edge of the horizontal bottom stopper next to the wall of centrifugation article 20. Comparing the results of Sample No. 1 with those of Sample No. 3, which again employed the liquid filter medium technique and a horizontal stopper but was performed using the three entry procedure, it is seen that the recovery rate in Sample No. 3 is greatly improved. This could be explained by the fact that because less relative centrifugal force was applied, the microbial pathogens did not become so tightly lodged in the crevice between the bottom stopper and the walls of article 20. Further, the 3 entry technique allows for recovery of all microbial pathogens which have been resuspended in the remaining portion of the blood sample. When the two entry procedure is employed some of attributed to the use of an angled bottom stopper positioned at an angle with respect to the walls of article 20 which is the complement of the angle at which article 20 was centrifuged. A comparison of Sample No. 10 to Sample No. 12 similarly illustrates the superior results obtained when using an angled bottom stopper at higher relative centrifugal forces (3000).

TABLE I

| Sample No. | Microbial Pathogen | Technique | Bottom Stopper | Number of Entries | RCF (Relative Centrifugal Force) | % Recovery |
|---|---|---|---|---|---|---|
| 1. | *Escherichia coli* | Liquid Filter Medium (50% Sucrose) | Horizontal | 2 | 1500 | 65 ± 11 |
| 2. | " | Liquid Filter Medium (50% Sucrose) | Horizontal | 2 | 3000 | 55 ± 5 |
| 3. | " | Liquid Filter Medium (50% Sucrose) | Horizontal | 3 | 1500 | 90 ± 4 |
| 4. | " | Liquid Filter Medium (60% Sucrose) | Horizontal | 2 | 3000 | 63 ± 14 |
| 5. | " | Liquid Filter Medium (60% Sucrose) | Horizontal | 3 | 1500 | 90 ± 3 |
| 6. | " | Liquid Filter Medium (60% Sucrose) | Horizontal | 3 | 3000 | 95 ± 15 |
| 7. | " | Cushioning Agent (Fluorinert FC-48) | Horizontal | 2 | 1500 | 65 ± 16 |
| 8. | " | Cushioning Agent (Fluorinert FC-48) | Horizontal | 2 | 3000 | 90 ± 7 |
| 9. | " | Cushioning Agent (Fluorinert FC-48) | Horizontal | 3 | 1500 | 81.5 ± 4 |
| 10. | " | Cushioning Agent (Fluorinert FC-48) | Horizontal | 3 | 3000 | 89 ± 2 |
| 11. | " | Cushioning Agent (Fluorinert FC-48) | Angled (Sylgard Plug) | 3 | 1500 | 98 ± 1.2 |
| 12. | " | Cushioning Agent (Fluorinert FC-48) | Angled (Sylgard Plug) | 3 | 3000 | 98 ± 1 |
| 13. | *Candida albicans* | Liquid Filter Medium (50% Sucrose) | Horizontal | 2 | 1500 | 38 ± 22 |
| 14. | " | Liquid Filter Medium (50% Sucrose) | Horizontal | 2 | 3000 | 40 ± 8 |
| 15. | " | Liquid Filter Medium (50% Sucrose) | Horizontal | 3 | 3000 | 53 ± 16 |
| 16. | " | Liquid Filter Medium (60% Sucrose) | Horizontal | 3 | 1500 | 92 ± 7 |
| 17. | " | Cushioning Agent (Fluorinert FC-48) | Horizontal | 3 | 3000 | 98 ± 6 |
| 18. | " | Cushioning Agent (Fluorinert FC-48) | Angled (Sylgard Plug) | 3 | 1500 | 99 ± 4 |
| 19. | " | Cushioning Agent (Fluorinert FC-48) | Angled (Sylgard Plug) | 3 | 3000 | 100 |
| 20. | " | Cushioning Agent (Fluorinert FC-48) | Angeled (Bathtub Calk Plug) | 3 | 1500 | 91 ± 16 |
| 21. | " | Cushioning Agent (Fluorinert FC-48) | Angled (Bathtub Caulk Plug) | 3 | 3000 | 99 ± 1 | the resuspended microbial pathogens may be left behind in the residual portion of the blood sample.

A comparison of Sample No. 15 with that of Sample No. 17 demonstrates the improved results possible when using the cushioning agent technique of the present invention. In Sample No. 15, as in Sample No. 17, a horizontal bottom stopper was employed, the number of entries was 3, and the relative centrifugal force was the same as in Sample No. 17 (3000). The improved results when using the cushioning agent technique is believed to result from the use of the cushioning agent which does not allow microbial pathogens to pass therethrough and become lost at the interface between the walls of article 20 and the bottom stopper.

Further, a comparison of Sample No. 9 with Sample No. 11 demonstrates the advantages obtained by employing an angle stopper as compared to the horizontal bottom stopper. Since the conditions and techniques in Samples No. 9 and 11 are exactly identical except for the fact that in Sample No. 11 an angle stopper was employed, the improvement present in recovery rate in Sample No. 11 over that of Sample No. 9 can only be While this invention has been described in relation to its preferred embodiments, it is to be understood that various modifications thereof will now be apparent to one skilled in the art upon reading this specification and it is intended to cover such modifications as fall within the scope of the appended claims.

I claim:

1. An article used for the concentration of microbial pathogens from a sample fluid comprising:
   an enclosed centrifugation receptacle sealably closed with injectable closure means, the interior of said receptacle comprising an evacuated spaced maintained at a lower than atmospheric pressure, adjacent a high density, non-toxic to microbial organisms, water immiscible, hydrophobic liquid cushioning agent capable of collecting substantially all of the microbial pathogens which pass out of suspension from said sample fluid without a loss of said microbial pathogens to interstitial spaces present in said centrifugation receptacle and wherein the density of the liquid cushioning agent is sufficient so as not to be supported by a mixture of a sample fluid and a treating fluid therefore.

2. The article of claim 1 wherein said cushioning agent is present in an amount equal to from about 4.7% to about 28.6% by volume.

3. The article of claim 2 wherein said cushioning agent comprises an inert, liquid fluorinated hydrocarbon having a density of from about 1.6 grams per cubic centimeter to about 2.0 grams per cubic centimeter.

4. The collecting agent of claim 3 wherein said liquid fluorinated hydrocarbon has a boiling point of from at least about 200 degrees F. to about 420 degrees F.

5. An article for the concentration of microbial pathogens contained in a blood sample comprising:
(a) an enclosed centrifugation receptacle having a first end and a second end, said ends being sealably closed with injectable closure means;
(b) an injectable plug adjacent the injectable closure means of said second end, said injectable plug comprising a surface disposed at an angle with respect to the interior of said centrifugation receptacle, said angle being the complement of the angle at which said article is to be centrifuged;
(c) an effective amount of a high density, non-toxic to microbial organisms, water immiscible, hydrophobic liquid cushioning agent contained within said centrifugation receptacle and wherein the cushioning agent is capable of collecting substantially all of the microbial pathogens which pass out of the suspension from said sample fluid without loss of said microbial pathogens to interstitial spaces present in said centrifugation receptacle and wherein the density of the liquid cushioning agent is sufficient so as not to be supported by a mixture of a sample fluid and a treating fluid therefore; and
(d) an effective amount of a non-toxic lysing agent contained within said centrifugation receptacle.

6. The article of claim 5, wherein said injectable plug is an extension of the injectable closure means of said second end of said centrifugation receptacle.

7. The article of claim 5 wherein said cushioning agent is present in an amount equal to from about 3.3% to about 30.0% by volume.

8. The article of claim 5 wherein the angle of the surface of said injectable plug with respect to the interior of said centrifugation receptacle is from about 30 degrees to about 80 degrees.

9. The article of claim 8 wherein said angle is 34 degrees.

10. The article of claim 5 wherein the angle of the surface of said injectable plug with respect to the interior of said centrifugation receptacle is about 90 degrees.

11. The article of claim 5 wherein said cushioning agent is an inert, liquid fluorinated hydrocarbon.

12. The cushioning agent of claim 11 wherein said fluorinated hydrocarbon has a density of at least 1.2 grams per cubic centimeter and a boiling point at least about 200 degrees F.

13. In an article for the concentration of microbial pathogens suspected to be present in a blood sample, comprising:
an enclosed centrifugation vessel having a first end and a second end;
a chamber containing an evacuated space maintained at a lower than atmospheric pressure; and
a first injectable closure means sealably closing the first end of said centrifugation vessel, the improvement comprising:
a second injectable closure means sealably closing said second end of said centrifugation vessel and comprising a surface disposed at an angle with respect to the interior of said elongated centrifugation receptacle, said angle being the complement of the angle at which said article is to be centrifuged; and
an effective amount of an inert, non-toxic to microbial organisms, high density, water immiscible, hydrophobic liquid cushioning agent contained within said chamber and wherein the cushioning agent is capable of collecting substantially all of the microbial pathogens which pass out of the suspension from said sample fluid without loss of said microbial pathogens to interstitial spaces present in said centrifugation receptacle and wherein the density of the liquid cushioning agent is sufficient so as not to be supported by a mixture of a sample fluid and a treating fluid therefore.

14. The improved article of claim 13 and further comprising an effective amount of blood treating agents selected from the group consistng of lysing agents, anticoagulants and mixtures thereof.

15. The article of claim 14 wherein said treating agents are present in an amount equal to at least about 1% by volume based on the volume of the treating agents, blood sample and cushioning agent.

16. The article of claim 15 wherein said treating agents are presnt in an amount equal to from about 7.6% to about 17.5% by volume.

17. The article of claim 14 wherein said treating agent comprises a detoxified saponin.

18. The article of claim 14 wherein said treating agent comprises sodium polyanothal sulfonate.

19. The article of claim 13 wherein said angle of the surface of the injectable closure means sealably closing said second end of said centrifugation vessel is from about 30 degrees to about 80 degrees.

20. The article of claim 19 wherein said angle is 34 degrees.

21. The article of claim 13 wherein said cushioning agent is present in an amount equal to from about 3.3% to about 30.0% by volume.

22. The article of claim 21 wherein said cushioning agent comprises a liquid fluorinated hydrocarbon having a density of from about 1.6 grams per cubic centimeter to about 2.0 grams per cubic centimeter, and a boiling point of at least about 200 degrees F.

* * * * *